US008168610B2

(12) United States Patent
Gleave et al.

(10) Patent No.: US 8,168,610 B2
(45) Date of Patent: *May 1, 2012

(54) BISPECIFIC OLIGONUCLEOTIDE FOR THE TREATMENT OF CNS MALIGNANCIES

(75) Inventors: Martin Gleave, Vancouver (CA);
Michael N. Pollak, Montreal (CA);
Randy J. Leavitt, Dollard-des-Ormeaux (CA)

(73) Assignee: The University of British Columbia, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/004,421

(22) Filed: Jan. 11, 2011

(65) Prior Publication Data

US 2011/0152354 A1 Jun. 23, 2011

Related U.S. Application Data

(63) Continuation of application No. 10/908,496, filed on May 13, 2005, now Pat. No. 7,932,234, which is a continuation-in-part of application No. PCT/CA2004/001778, filed on Sep. 30, 2004.

(60) Provisional application No. 60/507,128, filed on Oct. 1, 2003.

(51) Int. Cl.
*A01N 43/04* (2006.01)
*A61K 31/70* (2006.01)
*C07H 21/04* (2006.01)
*C12Q 1/68* (2006.01)
*C12N 5/00* (2006.01)

(52) U.S. Cl. ............ 514/44; 536/23.1; 536/24.5; 435/6; 435/375

(58) Field of Classification Search ............... None
See application file for complete search history.

(56) References Cited

U.S. PATENT DOCUMENTS

| 5,417,978 A | 5/1995 | Tari et al. |
| 5,646,042 A | 7/1997 | Stinchcomb et al. |
| 5,801,154 A | 9/1998 | Baracchini et al. |
| 5,855,911 A | 1/1999 | Lopez-Berestein et al. |
| 5,929,040 A | 7/1999 | Werther et al. |
| 5,994,320 A | 11/1999 | Low et al. |
| 5,998,148 A | 12/1999 | Bennett et al. |
| 6,284,741 B1 | 9/2001 | Werther et al. |
| 6,451,991 B1 | 9/2002 | Martin et al. |
| 2003/0045488 A1 | 3/2003 | Brown et al. |
| 2003/0087857 A1 | 5/2003 | Freier |
| 2003/0158143 A1 | 8/2003 | Gleave et al. |

FOREIGN PATENT DOCUMENTS

| WO | 92/03471 | 3/1992 |
| WO | 9203470 | 3/1992 |
| WO | 0069454 | 11/2000 |
| WO | 0078341 | 12/2000 |
| WO | 0105435 | 1/2001 |
| WO | 02/22642 | 3/2002 |
| WO | 03030826 | 4/2003 |
| WO | 03062421 | 7/2003 |

OTHER PUBLICATIONS

Nordqvist, et al. (2002) Expression of IGF-II, IGFBP-2, -5, and -6 in Meningiomas With Different Brain Invasiveness. J. Neuro-Onc., v.57:19-26.*
Wang, et al. (2006) Overexpression of IGFBP5, But Not IGFBP3, Correlates With the Histologic Grade of Human Diffuse Glioma: A Tissue Microarray and Immunohistochemical Study. Technology in Cancer Research and Treatment, V.5(3):195-9.*
Moore, et al. (2009) IGFBP2 is a Candidate Biomarker for INK4A-ARF Status and a Therapeutic Target for High-Grade Gliomas. Proc. Nat. Acad. Sci., v.106(39):16675-9.*
Lin, et al. (2009) Plasma IGFBP-2 Levels Predict Clinical Outcomes of Patients With High-Grade Gliomas. Neuro Oncol., v.11(5):468-76.*
Parkin et al., Estimating the World Cancer Burden: Globocan 2000, Int. J. Cancer, 2001, pp. 153-156, vol. 94.
National Cancer Institute, Trends in SEER Incidence and U.S. Mortality Using the Joinpoint Regression Program, 1975-2000 With Up to Three Joinpoints by Race and Sex, SEER Cancer Statistics Review 1975-2000, 2000, Publisher: National Cancer Institute.
Strother et al., Tumors of the Central Nervous System, Principles and Practice of Pediatric Oncology, 4th Edition, 2002, pp. 751-824, Editors: Pizzo et al., Publisher: Lippincott Williams & Wilkins.
Surawicz et al., Brain tumor survival: Results from the National Cancer Data Base, Journal of Neuro-Oncology, 1998, pp. 151-160, vol. 40.
Andress et al., Human Osteoblast-derived Insulin-like Growth Factor (IGF) Binding Protein-5 Stimulates Osteoblast Mitogenesis and Potentiates IGF Action, Journal of Biological Chemistry, 1992, pp. 22467-22472, vol. 267, No. 31.
Branch, Andrea D., A good antisense molecule is hard to find, TIBS, 1998, pp. 45-50.
Crooke et al., Basic Principles of Antisense Therapeutics, Antisense Research and Application, 2004, pp. 1-50, Publisher: Springer.
Jen et al., Suppression of Gene Expression by Targeted Disruption of Messenger RNA: Available Options and Current Strategies, Stem Cells 2000, 2000, pp. 307-319, vol. 18.
Agrawal et al., Antisense therapeutics: is it as simple as complementary base recognition?, Molecular Medicine Today, 2000, pp. 72-81, vol. 6.
Angelloz-Nichoud et al., Autocrine Regulation of Cell Proliferation by the Insulin-Like Growth Factor (IGF) and IGF Binding Protein-3 Protease System in a Human Prostate Carcinoma Cell Line (PC-3), Endocrinology, 1995, pp. 5485-5492, vol. 136, No. 12.

(Continued)

*Primary Examiner* — Jennifer Pitrak McDonald
(74) *Attorney, Agent, or Firm* — Larson & Anderson, LLC.

(57) ABSTRACT

CNS malignancy is treated in a subject suffering from a CNS malignancy by administering to the subject an antisense oligonucleotide having a sequence of bases that is complementary to portions of both the gene encoding IGFBP-2 and the gene encoding IGFBP-5, and which is of sufficient length to act as an inhibitor of the effective amount of IGFBP-2 and IGFBP-5, in an amount effective to reduce effective levels of IGFBP-2 and IGFBP-5 in cells of the CNS malignancy.

2 Claims, 1 Drawing Sheet

OTHER PUBLICATIONS

Boudon et al., Secretion of Insulin-Like Growth Factors and Their Binding Proteins by Human Normal and Hyperplastic Prostatic Cells in Primary Culture, Journal of Clinical Endocrinology and Metabolism, 1996, pp. 612-617, vol. 81, No. 2.

Cucco et al., In Vitro and in Vivo Reversal of Multidrug Resistance in a Human Leukemia-Resistant Cell Line by mdr1Antisense Oligodeoxynucleotides, Cancer Research, 1996, pp. 4332-4337, vol. 56.

Elgin et al., An insulin-like growth factor (IGF) binding protein enhances the biologic response to IGF-I, Cell Biology, 1987, pp. 3254-3258, vol. 84, Publisher: Proc. Natl. Acad Sci.

Tamm et al., Antisense therapy in oncology: new hope for an old idea?, The Lancet, pp. 489-497, vol. 358, No. 9280.

Agrawal, Antisense oligonucleotides: towards clinical trials, TIBTECH, 1996, pp. 376-387, vol. 14.

Gewirtz et al., Facilitating oligonucleotide deliver: Helping antisense deliver on its promise, Proc. Natl. Acad. Sci., 1996, pp. 3161-3163, vol. 93.

Gregory, Androgen Receptor Up-Regulates Insulin-Like Growth Factor Binding Protein-5 (IGFBP-5) Expression in a Human Prostate Cancer Xenograft, Endocrinology, 1999, pp. 2372-2381, vol. 140, No. 5.

Huynh et al., A Role for Insulin-like Growth Factor Binding Protein 5 in the Antiproliferative Action of the Antiestrogen ICI 182780, Cell Growth and Differentiation, 1996, pp. 1501-1506, vol. 7.

Nickerson et al., Castration-induced Apoptosis of Androgen-dependent Shionogi Carcinoma is Associated with Increased Expression of Genes, Cancer Research, 1999, pp. 3392-3395, vol. 59.

Reuters, Lilly, Isis Antisense Drug Fails in Trial, News Release, 2003.

Figueroa et al., Differential Expression of Insulin-Like Growth Factor Binding Proteins in High Versus Low Gleason Score Prostate Cancer, The Journal of Urology, 1998, pp. 1379-1383, vol. 159, No. 4.

Huynh et al., Estradiol and Antiestrogens Regulate a Growth Inhibitory Insulin-Like Growth Factor Binding Protein 3 Autocrine Loop in Human Breast Cancer Cells, The Journal of Biological Chemistry, 1996, pp. 1016-1021, vol. 271, No. 2.

Jansen et al., bcl-2 antisense therapy chemosensitizes human melanoma in SCID mice, Nature Medicine, 1998, vol. 4, No. 2.

Monia et al., Antitumor Activity of a Phosphorothioate Antisense Oligodeoxynucleotide Targeted against C-raf Kinase, Nature Medicine, 1996, pp. 668-675, vol. 2, No. 6.

Nickerson et al., Castration-induced apoptosis in the rat ventral prostate is associated with increased expression of genes encoding insulin-like growth factor binding proteins 2, 3, 4 and 5, Endocrinology, 1998, pp. 807-810, vol. 139, No. 2.

Oh et al., Management of Hormone Refractory Prostate Cancer: Current Standards and Future Prospects, The Journal of Urology, 1998, pp. 1120-1229, vol. 160, No. 4.

Oh et al., Insulin-like Growth Factor (IGF)-independent Action of IGF-binding Protein-3 in Hs578T Human Breast Cancer Cells, The Journal of Biological Chemistry, 1993, pp. 14964-14971, vol. 268, No. 20.

Rajaram, Insulin-like Growth Factor-Binding Proteins in Serum and Other Biological Fluids: Regulation and Functions, Endocrine Reviews, 1997, pp. 801-831, vol. 18, No. 6.

Damon et al., Over expression of an Inhibitory insulin-Like Growth Factor Binding Protein (IGFBP), IGFBP-4, Delays Onset of Prostate Tumor Formation, Endocrinology, 1998, pp. 3456-3464, vol. 139, No. 8.

Ziegler et al., Induction of Apoptosis in Small-Cell Lung Cancer Cells by an Antisense Oligodeoxynucleotide Targeting the Bcl-2 Coding, Journal of National Cancer Institute, 1997, vol. 89, No. 14.

Wen, P.Y. et al., (Abstract Only) Brain Metastases, Curr. Treat. Options Oncol., 2000, pp. 447-458, vol. 1(5).

Zumkeller, W. IGFs and IGF-Binding Proteins as Diagnostic Markers and Biological Modulators in Brain Tumors, Expert Rev. Mol Diagn., 2002, pp. 473-477, vol. 2(5).

Kalota, et al., Progress in the Development of Nucleic Acid Therapeutics, Handbook Exp. Pharm., 2006, pp. 173-196, vol. 173.

Crooke, Progress in Antisense Technology, Ann. Rev. Med., 2004, pp. 61-95, vol. 55.

Opalinska et al., Nucleic Acid Therapeutics: Basic Principles and Recent Applications, Nature Review Drug Discover, 2002, pp. 503-514, vol. 1.

IGFBP alignment [online]. [retrieved on Jun. 18, 2009]. Retrieved from the internet: <http://blast.ncbi.nlm.nih.gov/Blast.cgi>.

Nordqvist, et al., Expression of IGF-II, IGFBP-2, -5, and -6 in Meningiomas with Different Brain Invasiveness, J. Neuro-Onc., 2002, pp. 19-26, vol. 57.

Wang, et al, Overexpression of IGFBP5, but not IGFBP3, Correlates With the Histologic Grade of Human Diffuse Glioma: A Tissue Microarray and Immunohistochemical Study, Technology in Cancer Research and Treatment, 2006, pp. 195-199, vol. 5(3).

Moore, et al, IGFBP2 is a Candidate Biomarker for INK4A-ARF Status and a Therapeutic Target for High-Grade Gliomas, Proc. Nat. Acad. Sci., 2009, pp. 16675-166759, vol. 106(39).

Lin, et al., Plasma IGFBP-2 Levels Predict Clinical Outcomes of Patients with High-Grade Gliomas, Neuro Oncol., 2009, pp. 468-476, vol. 11(5).

Levitt Jr. et al, Bispecific antisense oligonucleotide targeting both IGFBP-2 and IGFBP-5 inhibits growth of U87 glioma cells, Growth Hormone & IGF Research, Apr. 2004, p. 118, vol. 14, No. 2.

Miyake, et al., Castration-induced Up-Regulation of Insulin-like Growth Factor Binding Protein-5 Potentiates Insulin-like Growth Factor-I Activity and Accelerates Progression to Androgen Independence in Prostate Cancer Models, Cancer Research, Jun. 1, 2000, pp. 3058-3064, vol. 60.

Miyake, et al., Overexpression of Insulin-like Growth Factor Binding Protein-5 Helps Accelerate Progression to Androgen-independence in the Human Prostate LNCaP Tumor Model Through Activation of Phosphatidylinositol 3'-Kinase Pathway, Endocrinology, 2000, pp. 2257-2265, vol. 141, No. 6.

Bruchovsky et al., Classifiction of Dependent and Autonomous Variants of Shionogi Mammary Carcinoma Based on Heterogenous Patterns of Androgen Binding, Cell, 1978, pp. 273-280, vol. 13.

Bruchovsky et al., Effects of Androgen Withdrawal on the Stem Cell Composition of the Shionogi Carcinoma, Cancer Research, 1990, pp. 2275-2282, vol. 50.

Gleave et al., Serum Prostate Specific Antigen Levels in Mice Bearing Human Prostate LNCaP Tumors Are Determined by Tumor Volume and Endocrine and Growth Factors, Cancer research, 1992, pp. 1598-1605, vol. 52.

Gleave et al., Animal Models in Prostate Cancer, Principles and Practice of Genitourinary Oncology, 1997, pp. 367-378, Publisher: Lippincott-raven; Editors: Raghavan et al.

Gleave et al., Intermittent Androgen Suppression for Prostate Cancer; Rationale and Clinical Experience, European Urology, 1998, pp. 37-41, vol. 34; Suppl. 3.

Gleave et al., Prostate cancer: 9, Treatment of advanced disease, Canadian Medical Association Journal, 1999, pp. 225-232, vol. 160, No. 2.

Gleave et al., Neoadjuvant Androgen Withdrawal Therapy Decreases Local Recurrence Rates Following Tumor Excision in the Shiongi Tumor Model, The Journal of Urology, 1997, pp. 1727-1730, vol. 157, No. 5.

Gleave et al., Antisense Targets to Enhance Hormone and Cytotoxic Therapies in Advanced Prostate Cancer, Current Drug Targets, 2003, pp. 209-221, vol. 4, No. 3.

James et al., A Highly Conserved Insulin-like Growth Factor-binding Protein (IGFBP-5) is Expressed during Myoblast Differentiation, The Journal of Biological Chemistry, 1993, pp. 22305-22312, vol. 268, No. 30.

Kiefer et al., Molecular cloning of a New Human Insulin-like Growth Fator Binding Protein, Biochemical and Biophysical Research Communications, 1991, pp. 219-225, vol. 176, No. 1.

Rennie et al., Gene Expression during the Early Phases of Regression of the Androgen-dependent Shionogi Mouse Mammary Carcinoma, Cancer Research, 1988, pp. 6309-6312, vol. 48.

Binkert, et al., Structure of the Human Insulin-Like Growth factor Binding Protein-2 Gene, Molecular Endocrinology, 1992, pp. 826-836, vol. 6, No. 5.

Bubendorf, et al., Hormone Therapy Failure in Human Prostate Cancer: Analysis by Complementary DNA and Tissue Microarrays, Journal of the National Cancer Institute, 1999, pp. 1758-1764, vol. 91.

Corkins et al., Growth Stimulation by Transfection of Intestinal Epithelial Cells with an Antisense Insulin-Like Growth Factor Binding Protein-2 Construct, Biochemical and Biophysical Research Communications, 1995, pp. 707-713, vol. 211, No. 3.

Forsyth, et al., Growth Inhibition of a Human colon Cancer Cell Line by Antisense Oligonucleotide to IGFBP-2, 1995, p. A726, vol. 108, No. 4.

Steller et al., Insulin-like growth factor II mediates epidermal growth factor-induced mitogenesis in cervical cancer cells, Proc. Natl. Acad. Sci. Cell Biology, 1995, pp. 11970-11974, vol. 92.

Wang et al., Correlation of Glioma Cell Regression with Inhibition of Insulin-Like Growth Factor 1 and Insulin-Like Growth Factor-Binding Protein-2 Expression, Neuroendrocrinology, 1997, pp. 203-211: vol. 66.

Wang et al., Insulin-like growth factor binding protein 2 enhances glioblastoma invasion by activating invasion-enhancing genes, Cancer Research, 2003, pp. 4315-4321, vol. 63, No. 15.

Elmlinger, et al. "In vivo expression of insulin-like growth factor-binding protein-2 in human gliomas increases with the tumor grade." Endocrinology, 2001, pp. 1652-1658, vol. 142, No. 4.

Fuller, et al. "Overexpression of IGFBP5, but not IGFBP3, correlates with the histologic grade of human diffuse gliomas." Modern Pathology, 2003, p. 290a, vol. 16, No. 1.

Fuller, et al, "Reactivation of insulin-like growth factor binding protein 2 expression in glioblastoma multiframe: A revelation by parallel gene expression profiling." Cancer Research, 1999, pp. 4228-4232, vol. 59, No. 17.

Sallinen, et al "Identification of differentially, expressed genes in human gliomas by DNA micoarray and tissue chip techniques." Cancer Research, 2000, pp. 6617-6622, vol. 60, No. 23.

American Cancer Society, Cancer Facts & Figures 2004, 2004, pp. 1-56, Publisher: American Cancer Society.

Johnson et al., Quality of long-term survival in young children with medulioblastoma, J. Neurosurg., 1994, pp. 1004-1010, vol. 80.

Lallana et al., Update on the therapeutic approaches to brain tumors, Expert Rev. Anticancer Ther., 2003, pp. 655-670, vol. 3, No. 5.

Mahaley et al., National survey of patterns of care for brain-tumor patients, J. Neurosurg., 1989, pp. 826-836, vol. 71.

Packer et al., A prospective study of cognitive function in children receiving whole-brain radiotherapy and chemotherapy: 2-year results, J. Neurosurg., 1989, pp. 707-713, vol. 70.

* cited by examiner

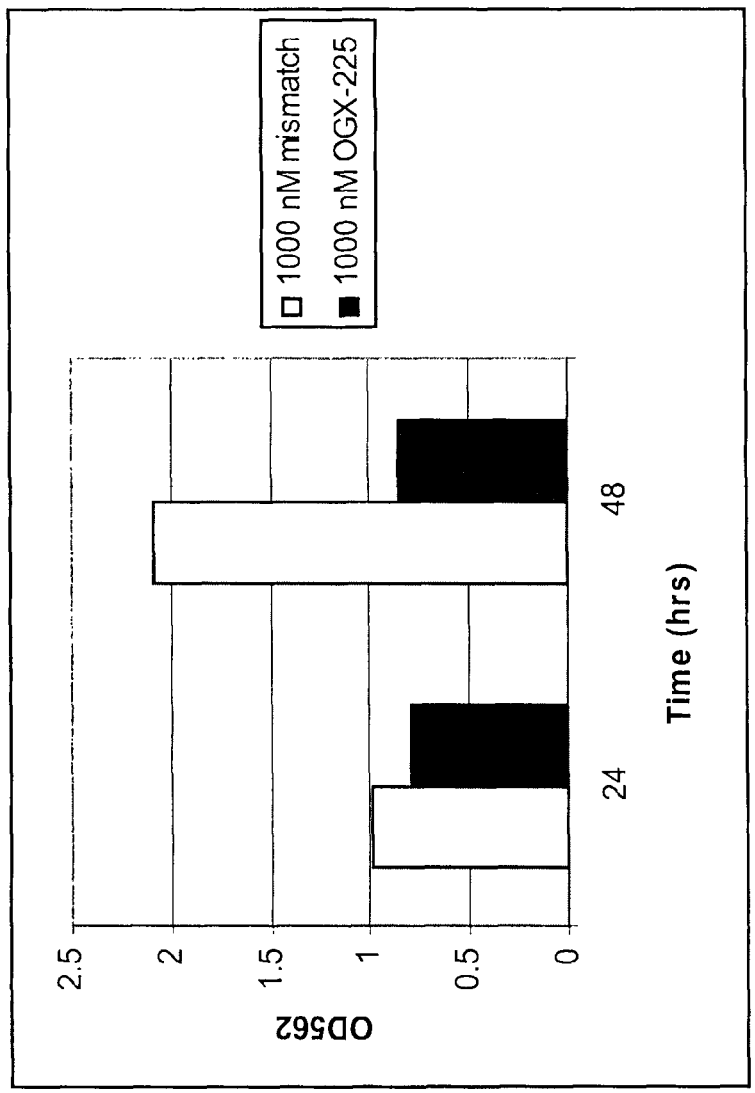

BISPECIFIC OLIGONUCLEOTIDE FOR THE TREATMENT OF CNS MALIGNANCIES

STATEMENT OF RELATED APPLICATIONS

This application is a continuation-in-part of PCT Patent Application PCT/CA2004/001778, filed Sep. 30, 2004 designating the United States, and claims the benefit of U.S. Provisional Application No. 60/507,128, filed Oct. 1, 2003, both of which are incorporated herein by reference.

FIELD OF THE INVENTION

This present application relates to antisense olignucleotides for the treatment of central nervous system malignancies.

BACKGROUND OF THE INVENTION

Cancer of the central nervous system (CNS), including the brain, meninges and spinal cord, ranks as the 12th most common malignancy diagnosed in men and the 15th most common in women, with 30% higher incidence in men. It is estimated that there will be 18,400 new cases and 12,690 deaths from brain and other nervous system tumors in the United States in 2004.[1] The combined incidence of primary invasive CNS tumors in that country is 6.6 per 100,000 persons per year, with an estimated mortality of 4.7.[2] Worldwide, approximately 176,000 new cases of brain and other CNS tumors were diagnosed in the year 2000, with an estimated mortality of 128,000.[3]

The pediatric situation is more bleak than that of adult CNS malignancy because of the higher incidence in that age group. CNS malignancies represent almost 17% of all malignancies during childhood according to United States data. CNS cancer as a group was the second most frequent malignancy of childhood and the most common of the solid tumors.

The seriousness and treatability of primary brain malignancies is determined by a number of variables including histology, size of tumor, extent of the malignancy, the patient's age and performance status, and the duration of symptoms.[4] Some primary brain tumors are curable by surgery alone, or by surgery and radiation therapy combined; but the remainder are not usually curable despite all the therapies combined.[5]

Further, while radiation therapy can be debilitating in adults, the use of radiation in treating pediatric brain tumors is not only technically demanding but more importantly, is debilitating in terms of growth and neurologic development. [6,7] Very young children with CNS cancer, especially infants with ependymoma or PNET, have low survival rates.

Alternative treatments for CNS malignancy are needed to provide new avenues of treatment.

PCT publication WO 00/69454 discloses the use of IGFBP-2 modulators to inhibit cancer.

PCT publication WO 00/78341 discloses a method for the prophylaxis and/or treatment of disorders related to insulin growth factor-I.

PCT publication WO 01/05435 describes a method for treating hormone-regulated tumors (for example, breast and prostatic tumors) by administration of an antisense oligodeoxynucleotide which is complementary to a portion of the gene encoding IGFBP-5.

PCT publication WO 02/22642 describes a method as provided for the treatment of prostate and other endocrine tumors by administration of an antisense oligodeoxynucleotide which is complementary to a portion of the gene encoding IGFBP-2.

United States published patent application US-2003-0158143-A1 describes the use of bispecific IGFBP-2/5 antisense oligonucleotides, especially for the treatment of endocrine-related tumors.

United States published patent application US 2003-0087857-A1 describes antisense modulation of IGFBP-5 expression

SUMMARY OF THE INVENTION

The present invention provides a method for treating a CNS malignancy in a subject suffering from a CNS malignancy, by administering to the subject an antisense oligonucleotide consisting essentially of a sequence of bases that is complementary to portions of both the gene encoding IGFBP-2 and the gene encoding IGFBP-5, and which is of sufficient length to act as an inhibitor of the effective amount of IGFBP-2 and IGFBP-5, in an amount effective to reduce effective levels of IGFBP-2 and IGFBP-5 in cells of the CNS malignancy. The amount of the antisense oligonucleotide administered may be between 300 mg and 750 mg, or between 10 mg and 100 mg depending on the mode and frequency of administration. The antisense oligonucleotide may be administered intratumorally, intrathecally, regional to the CNS malignancy, or systemically, or in a combination of ways. Further, the antisense oligonucleotide may be administered in combination with a chemotherapeutic agent, in combination with radiotherapy, or with surgery, or in combination of some or all of the therapies.

According to another aspect of the invention, there is provided a method for inducing apoptosis in glioma cells by contacting said cells with an antisense oligonucleotide consisting essentially of a sequence of bases that is complementary to portions of both the gene encoding IGFBP-2 and the gene encoding IGFBP-5, and which is of sufficient length to act as an inhibitor of the effective amount of IGFBP-2 and IGFBP-5.

The CNS malignancy may be a glioma, and the mammal may be a human for all aspects of the invention.

Other aspects and features of the present invention will become apparent to those ordinarily skilled in the art upon review of the following description of specific embodiments of the invention in conjunction with the accompanying figures.

BRIEF DESCRIPTION OF THE DRAWING

FIG. 1 shows a graphical representation of the results of the MTT assay of U87 glioma cells treated with 1000 nM antisense (MOE modified Seq. ID NO. 5) with Oligofectamine™ transfection reagent, or 1000 nM of mismatched control oligonucleotide, in serum-free Opti-MEM™ media.

DETAILED DESCRIPTION OF THE INVENTION

Definitions

The present invention provides bispecific antisense oligonucleotides which comprise a sequence of bases that is complementary to portions of both the gene encoding IGFBP-2 and the gene encoding IGFBP-5, and that is sufficient in length to act as an inhibitor of the effective amount of IGFBP-2 and/or IGFBP-5 (in general at least 14 bases) for pharmaceutical and research applications.

As used in the specification and claims of this application, the phrase "a sequence of bases that is complementary to both the gene encoding IGFBP-2 and the gene encoding IGFBP-5" refers to a common sequence of bases in which the same bases that are complementary to the IGFBP-2 gene are also complementary to the IGFBP-5 gene, as opposed to a sequence in which distinct portions of the oligonucleotide are separately complementary to the two genes. The invention does not, however, exclude minor modifications in sequence, such as the addition of one or two terminal bases, or single base substitutions which might depart from perfect complementarity, but which still function as an inhibitor of the effective amount of IGFBP-2 and IGFBP-5.

"Sufficient length to act as an inhibitor" means that the antisense comprises as many bases as required to reduce the levels of IGFBP-2 and IGFBP-5, usually from 10 to 30 bases, preferably 14-21 bases.

As used in the specification and claims of this application, the phrase "treating a CNS malignancy" refers to administration of antisense as defined to an individual diagnosed with or suffering from a CNS malignancy with the expectation that it will result in a reduction in the severity of the malignancy, or delay the progression of the malignancy. Treatment does not require a cure. Further, it will be appreciated that not all patients respond equally to therapeutics, and therefore an actual response from every patient, or from a given individual patient is not required for treatment to have occurred.

"CNS malignancy" refers to a primary cancer, neoplasm or tumor of the brain or related tissues that grows in an uncontrolled manner, possibly invading nearby tissue and/or metastasizing (spreading) to other sites via the bloodstream. Gliomas refer to tumors that begin in the glial (supportive) tissue of the CNS. The most common gliomas include astrocytomas, ependymomas, oligodendrogliomas, and tumors with mixtures of two or more of these cell types. CNS malignancy may be used interchangeably with "tumor", or "brain cancer".

Specific CNS malignancies suitable for treatment using the compositions and methods of the invention include, but are not limited to: astrocytic tumors such as juvenile pilocytic, subependymal, well differentiated or moderately differentiated anaplastic astrocytoma; anaplastic astrocytoma; glioblastoma multiforme; ependymal tumors such as myxopapillary and well-differentiated ependymoma, anaplastic ependymoma, ependymoblastoma; oligodendroglial tumors including well-differentiated oligodendroglioma and anaplastic oligodendroglioma; mixed tumors such as mixed astrocytoma-ependymoma, mixed astrocytoma-oligodendroglioma, mixed astrocytomaependymoma-oligodendroglioma; medulloblastoma; and any other infiltrating or non-infiltrating CNS tumors or cancers.

The antisense oligonucleotides of the invention may be referred to throughout the application as "antisense", "oligonucleotide", "antisense oligodeoxynucleotide", or "bispecific antisense oligonucleotide."

Antisense Oligodeoxynucleotides

Insulin-like growth factor-binding proteins (IGFBPs) are mediators in the biological response to insulin-like growth factor (IGF). To date, six IGFBPs have been identified whose function is believed to involve modulation of the biological actions of the IGF through high affinity interactions. [8] However, some evidence suggests biological activity for IGFBPs that is independent of IGFs [9,10], and both stimulatory and inhibitory effects of IGFBPs on cell proliferation have been reported under various experimental conditions. [9,11,12,13] Thus, the precise role of IGFBPs remains controversial.

Antisense oligonucleotides may function by different mechanisms. The effective amount of IGFBP-2 or IGFBP-5 is the amount that is present in a functional state in the cell. Reduction of this amount by administration of antisense oligonucleotides may occur through restricting production of the IGFBP (at the transcription or translation level) or by degrading the IGFBP at a rate faster than it is being produced. Further, it will be appreciated that inhibition occurs when the IGFBP would otherwise be present if the antisense oligonucleotide had not been administered.

Antisense oligonucleotides are stretches of single-stranded DNA, usually chemically modified, whose sequence (3' to 5') is complementary to the sense sequence of a molecule of mRNA. Antisense molecules thereby effectively inhibit gene expression by forming RNA/DNA duplexes [14], and offer a more targeted option for cancer therapy than chemotherapy or radiation. Antisense is believed work by a variety of mechanisms, including physically blocking the ability of ribosomes to move along the messenger RNA, and hastening the rate at which the mRNA is degraded within the cytosol.

Antisense oligodeoxynucleotides (ODNs) are synthetic polymers made up of monomers of deoxynucleotides like those in DNA. In the present application, the term antisense oligonucleotides includes antisense oligodeoxynucleotides.

In order avoid digestion by DNAse, antisense oligonucleotides and ODNs are often chemically modified. For example, phosphorothioate oligodeoxynucleotides are stabilized to resist nuclease digestion by substituting one of the non-bridging phosphoryl oxygen of DNA with a sulfur. Increased antisense oligonucleotide stability can also be achieved using molecules with 2-methoxyethyl (MOE) substituted backbones as described generally in U.S. Pat. No. 6,451,991, incorporated by reference in those jurisdictions allowing such incorporation, and US Patent Published patent application US-2003-0158143-A1.

The antisense oligonucleotide may be a 5-10-5 gap-mer methoxyl ethyl modified (MOE) oligonucleotide corresponding to SEQ ID NO.:5 below.

Specific antisense oligonucleotides according to the invention consist essentially of a series of bases as set forth in SEQ ID NO:1-7.

| SEQ. ID NO. | Sequence |
|---|---|
| 1 | GGTGTAGACGCCGCACG |
| 2 | GCAGCGCAGCCCCTGG |
| 3 | GCAGCAGCCGCAGCCCGGCTCC |
| 4 | AGCCGCAGCCCGGCTCCT |
| 5 | CAGCAGCCGCAGCCCGGCTC |
| 6 | GCAGCAGCCGCAGCCCGGCT |
| 7 | AGCAGCCGCAGCCCGGCTCC |

The compositions of the present invention can be used for treatment of CNS malignancies in mammals, including humans, by administration of a bispecific antisense oligonucleotide in accordance with the invention. Administration of antisense oligonucleotides can be carried out using the various mechanisms known in the art, including naked administration, and administration in pharmaceutically acceptable carriers. For example, lipid carriers for antisense delivery are described in U.S. Pat. Nos. 5,855,911 and 5,417,978 which are incorporated herein by reference in those jurisdictions allowing such incorporation.

Administration

The treatment of primary brain tumors in children and adults requires different approaches in terms of dosages, treatment regimens, and supportive therapies. [15]

In general, the antisense oligonucleotide is administered by intravenous, intraperitoneal, intratumor, via the cerebral spinal fluid by lumbar puncture or Ommaya reservoir (a device with a fluid reservoir that is surgically implanted under the scalp with a catheter into a ventricle of the brain), subcutaneous or oral routes. Where the oligonucleotides are administered in a pharmaceutically acceptable carrier, the carrier is generally free from substances which produce toxic or other harmful reactions when administered to humans.

Suitable carriers may include specialized delivery vehicles useful for nucleic acid delivery including lipid-based vehicles such as liposomes, the compositions of which may include other active components such as transfection aids. Such lipid vehicles include Oligofectamine™ which is commercially available.

One challenge for delivery of any therapeutic designed for the brain is the specialized barrier, the "blood brain barrier" (BBB), that protects the brain from viruses and many chemicals. The walls of the vessels that carry blood into the brain form the barrier. Leaky blood vessels in the body allow many molecules to cross through to tissue, but the tight construction of the vessels in the brain normally guards against entry for all but blood gases such as oxygen and small nutritional molecules.

The BBB can be overcome by conjugating the therapeutic onto molecules that already have brain access, for example docosahexaenoic acid (DHA). Alternately, the antisense may be conjugated to a targeting ligand present in the brain, such as insulin, transferrin, insulin-like growth factor I (IGF-I), insulin-like growth factor II (IGF-II), basic albumin, leptin, or prolactin. The targeting ligand may be an antibody that specifically binds to an insulin receptor, a transferrin receptor, an insulin-like growth factor I (IGF-IR) receptor, and insulin-like growth factor II receptor (IGF-IIR), or a leptin receptor.

Another method of promoting the delivery of a therapeutic across the BBB is BBB disruption, wherein the sugar mannitol or arabinose is used to cause the cells that line the vessel walls to shrink temporarily allowing a therapeutic to flow past the BBB to the brain tissue. For the purpose of improving the transfer of intravenously administered antisense across the blood brain barrier, various adjuvant agents such as those described above may be used.

In addition to being administered systemically, the antisense may also be administered directly into the malignancy, into the vasculature of the malignancy, into the region of the malignancy or into the cerebrospinal fluid (intrathecally). The amount of antisense oligonucleotide administered is one effective to reduce the effective amount of levels of IGFBP-2 and/or IGFBP-5 in the tumor cell of concern. As noted above, in the context of the present invention, applicants do not intend to be bound by any specific mechanism by which this reduction may occur, although it is noted that the reduction may occur as a result of reduced expression of IGFBP-2 and IGFBP-5 if the antisense molecule interferes with translation of the mRNA, or via an RNase mediated mechanism.

Specifically, a dose range of between 300 mg and 750 mg may be selected in the case of systemic administration, and the antisense oligonucleotide administered intravenously, for example, 1-3 times a week. The antisense oligonucleotide might for example be administered 3 times during week one and then weekly thereafter, until the desired clinical endpoint.

In the case of intratumoral, intraregional, tumor vasculature, or CSF administration (intrathecal administration), the dosage will be lower, for example the dose range may be between 10 and 100 mg, or continuously infused intrathecally at rates of 1-5 mg/kg/day. It will be appreciated that the appropriate therapeutic amount will vary both with the effectiveness of the specific antisense oligonucleotide employed, and with the nature of any carrier used. The determination of appropriate amounts for any given composition is within the skill in the art, through standard series of tests designed to assess appropriate therapeutic levels.

The method for treating CNS malignancies in accordance with the invention may further include administration of chemotherapy agents and/or additional antisense oligonucleotides directed at different targets. For example, conventional chemotherapy agents such as taxol (paclitaxel or docetaxel) and mitoxanthrone may be used. Similarly, combinations of the bispecific antisense oligonucleotide of the invention with other antisense sequences such as antisense Bcl-2 oligonucleotide, TRPM-2 (clusterin) oligonucleotide, IGFBP-2 or IGFBP-5 oligonucleotide may be used.

The methods of the invention may also include the use of radiotherapy before, during, or after the administration of the antisense therapeutic. Therapy involving surgically implanted carmustine-impregnated polymer combined with postoperative external beam radiation has been used in the treatment of high-grade gliomas. Dexamethasone, mannitol, and furosemide may be used to treat the peritumoral edema associated with brain tumors. Patients may also require treatment with corticosteroids, particularly if they are receiving radiation therapy. [16]

The application is further described in the following non-limiting examples. In each of these examples, the antisense employed is a 5-10-5 methoxy ethyl (MOE)-modified gapmer having the nucleic acid sequence of Seq. ID No. 5, which is referred to herein as "test antisense".

EXAMPLE 1

Growth Inhibition of U87 Glioma Cells by Bispecific Antisense

The effect of the test antisense, a bispecific antisense oligonucleotide targeting both IGFBP-2 and -5, on the high-grade glioma cell line U87, was examined. The choice of cell line was based on the fact that microarray gene expression studies, IGFBP-2 is significantly overexpressed in high grade gliomas. Treatment of U87 cells with 1000 nM test antisense for 48 hrs resulted in a ~70% decrease in cell viability when compared to 1000 nM mismatch control.

EXAMPLE 2

Test Antisense Downregulates the Expression of Both IGFBP-2 and IGFBP-5

Western blots were performed on concentrated conditioned media collected from U87 glioma cells treated for 48 hrs with 1000 nM mismatch control oligo or 1000 nM test antisense in serum-free Opti-MEM™ media. Growth inhibition by test antisense was associated with decreased production of both IGFBP-2 and IGFBP-5 in the conditioned media.

EXAMPLE 3

Test Antisense Induces Apoptosis

Western blots were performed on whole cell lysates collected from U87 glioma cells treated for 24 hrs with 1000 nM mismatch control oligonucleotide or 1000 nM test antisense in serum-free Opti-MEM™ media. Poly(ADP-ribose) polymerase (PARP) cleavage as measured by Western blotting revealed that test antisense induced apoptosis in U87. Alpha-tubulin levels acted as a control.

EXAMPLE 4

Test Antisense Performs Better than Monospecific Antisense Oligonucleotides

IGFBP-2 and IGFBP-5 monospecific antisense oligonucleotides were tested in prostate, LNCaP and PC3 cells alongside the bispecific oligonucleotide test antisense. Test antisense demonstrated better activity than either of the monospecific antisense oligonucleotides alone.

EXAMPLE 5

Treatment of Patients with Glioma

Patients presenting with glioma are injected intravenously or into the cerebral spinal fluid with test antisense in sterile saline at doses of 300 mg to 750 mg (depending on the weight, age and gender of the patient) on day one, day three and day seven, then weekly until a satisfactory reduction in tumor size is noted. While specific embodiments of the invention have been described and illustrated, such embodiments should be considered illustrative of the invention only and not as limiting the invention.

All of the cited documents are incorporated herein by reference.

REFERENCES

1. American Cancer Society.: Cancer Facts and Figures 2004. Atlanta, Ga.: American Cancer Society, 2004.
2. Trends in SEER incidence and U.S. mortality using the joinpoint regression program 1975-2000 with up to three joinpoints by race and sex. In: Ries L A G, Eisner M P, Kosary C L, et al.: SEER Cancer Statistics Review, 1975-2000. Bethesda, Md.: National Cancer Institute, 2003, Section 3: Brain and Other Nervous System Cancer (Invasive), Table III-1.
3. Parkin D M, Bray F, Ferlay J, et al.: Estimating the world cancer burden: Globocan 2000. Int J Cancer 94(2): 153-6, 2001.
4. Mahaley M S, Mettlin C, Natarajan N, et al.: National survey of patterns of care for brain tumor patients. J Neurosurg 71(6): 826-36, 1989.
5. Surawicz T S, Davis F, Freels S, et al.: Brain tumor survival: results from the National Cancer Data Base. J Neurooncol 40(2): 151-60, 1998.
6. Packer R J, Sutton L N, Atkins T E, et al.: A prospective study of cognitive function in children receiving whole-brain radiotherapy and chemotherapy: 2-year results. J Neurosurg 70(5): 707-13, 1989.
7. Johnson D L, McCabe M A, Nicholson H S, et al.: Quality of long-term survival in young children with medulloblastoma. J Neurosurg 80(6): 1004-10, 1994.
8. Rajaram et al., Endocrin. Rev. 18: 801-813 (1997).
9. Andress et al., J. Biol. Chem. 267: 22467-22472 (1992).
10. Oh et al., J. Biol. Chem. 268: 14964-14971 (1993).
11. Elgin et al., Proc. Nat'l. Acad. Sci. (USA), 84, 3254-3258 (1987).
12. Huynh et al., J. Biol. Chem. 271: 1016-1021 (1996)
13. Damon et al., Endocrinology 139: 3456-3464 (1998).
14. Figueroa, et al., J. Urol., 159: 1379-1383 (1998).
15. Strother D R, Poplack I F, Fisher P G, et al.: Tumors of the central nervous system. In: Pizzo P A, Poplack D G, eds.: Principles and Practice of Pediatric Oncology. 4th ed. Philadelphia, Pa.: Lippincott, Williams and Wilkins, 2002, pp 751-824; and (2).
16. Lallana E C, Abrey L E: Update on the therapeutic approaches to brain tumors. Expert Rev Anticancer Ther 3(5): 655-70, 2003.

What is claimed is:

1. A method for inducing apoptosis in glioma cells comprising contacting said cells with an antisense oligonucleotide, wherein substantially all of the antisense oligonucleotide is complementary to a portion of a gene encoding IGFBP-2 and substantially all of the antisense oligonucleotide is also complementary to a gene encoding IGFBP-5, and wherein the antisense oligonucleotide is of sufficient length to act as an antisense inhibitor of IGFBP-2 and IGFBP-5, and wherein the antisense oligonucleotide consists of the sequence as set forth in any one of Seq. ID Nos. 1 to 7.

2. The method of claim 1, wherein the antisense oligonucleotide consists of the sequence as set forth in Seq. ID No. 5.

* * * * *

SEQUENCE LISTING

```
<160> NUMBER OF SEQ ID NOS: 7

<210> SEQ ID NO 1
<211> LENGTH: 17
<212> TYPE: DNA
<213> ORGANISM: Artificial Sequence
<220> FEATURE:
<223> OTHER INFORMATION: antisense

<400> SEQUENCE: 1
ggtgtagacg ccgcacg                                                    17

<210> SEQ ID NO 2
<211> LENGTH: 16
<212> TYPE: DNA
<213> ORGANISM: Artificial Sequence
<220> FEATURE:
<223> OTHER INFORMATION: antisense

<400> SEQUENCE: 2
gcagcgcagc ccctgg                                                     16

<210> SEQ ID NO 3
<211> LENGTH: 22
```

```
<212> TYPE: DNA
<213> ORGANISM: Artificial Sequence
<220> FEATURE:
<223> OTHER INFORMATION: antisense

<400> SEQUENCE: 3
gcagcagccg cagcccggct cc                                           22

<210> SEQ ID NO 4
<211> LENGTH: 18
<212> TYPE: DNA
<213> ORGANISM: Artificial Sequence
<220> FEATURE:
<223> OTHER INFORMATION: antisense

<400> SEQUENCE: 4
agccgcagcc cggctcct                                                18

<210> SEQ ID NO 5
<211> LENGTH: 20
<212> TYPE: DNA
<213> ORGANISM: Artificial Sequence
<220> FEATURE:
<223> OTHER INFORMATION: antisense

<400> SEQUENCE: 5
cagcagccgc agcccggctc                                              20

<210> SEQ ID NO 6
<211> LENGTH: 20
<212> TYPE: DNA
<213> ORGANISM: Artificial Sequence
<220> FEATURE:
<223> OTHER INFORMATION: antisense

<400> SEQUENCE: 6
gcagcagccg cagcccggct                                              20

<210> SEQ ID NO 7
<211> LENGTH: 20
<212> TYPE: DNA
<213> ORGANISM: artificial sequence
<220> FEATURE:
<223> OTHER INFORMATION: antisense

<400> SEQUENCE: 7
agcagccgca gcccggctcc                                              20
```